(12) United States Patent
Lipkens et al.

(10) Patent No.: US 9,725,710 B2
(45) Date of Patent: Aug. 8, 2017

(54) ACOUSTOPHORESIS DEVICE WITH DUAL ACOUSTOPHORETIC CHAMBER

(71) Applicant: FloDesign Sonics, Inc., Wilbraham, MA (US)

(72) Inventors: Bart Lipkens, Hampden, MA (US); Brian McCarthy, Ludlow, MA (US); Ben Ross-Johnsrud, Wilbraham, MA (US); Jason Barnes, Westfield, MA (US); Dane Mealey, Springfield, MA (US); Thomas J. Kennedy, III, Wilbraham, MA (US)

(73) Assignee: FloDesign Sonics, Inc., Wilbraham, MA (US)

( * ) Notice: Subject to any disclaimer, the term of this patent is extended or adjusted under 35 U.S.C. 154(b) by 0 days.

(21) Appl. No.: 14/592,337

(22) Filed: Jan. 8, 2015

(65) Prior Publication Data

US 2015/0191716 A1 Jul. 9, 2015

Related U.S. Application Data

(60) Provisional application No. 61/925,171, filed on Jan. 8, 2014.

(51) Int. Cl.
*C12N 13/00* (2006.01)
*B01D 21/28* (2006.01)
*A61L 2/00* (2006.01)
*B06B 1/00* (2006.01)
*C22B 3/00* (2006.01)
(Continued)

(52) U.S. Cl.
CPC .......... *C12N 13/00* (2013.01); *B01D 21/283* (2013.01)

(58) Field of Classification Search
CPC ................... B01D 17/06; C02F 1/36
See application file for complete search history.

(56) References Cited

U.S. PATENT DOCUMENTS

| 2,667,944 A | 2/1954 | Crites |
| 3,555,311 A | 1/1971 | Weber |
| 4,055,491 A | 10/1977 | Porath-Furedi |

(Continued)

FOREIGN PATENT DOCUMENTS

| DE | 30 27 433 A1 | 2/1982 |
| EP | 0 292 470 B1 | 11/1988 |

(Continued)

OTHER PUBLICATIONS

International Search Report and Written Opinion for International Application No. PCT/US2015/010595 dated Apr. 15, 2015.
(Continued)

*Primary Examiner* — Krishnan S Menon
*Assistant Examiner* — Ryan B Huang
(74) *Attorney, Agent, or Firm* — Richard M. Klein; Fay Sharpe LLP

(57) ABSTRACT

An acoustophoresis device includes an acoustic chamber with a piezoelectric element located within its volume. The piezoelectric element vibrates and generates acoustic standing waves from both sides, so that particles can be separated from fluid passing through the acoustic chamber. This permits the element to be cooled more efficiently, reducing transient heat loads in the fluid traveling through the device.

22 Claims, 10 Drawing Sheets

(51) Int. Cl.
C22B 9/00 (2006.01)
B03B 5/00 (2006.01)

(56) References Cited

U.S. PATENT DOCUMENTS

| | | | |
|---|---|---|---|
| 4,165,273 A | 8/1979 | Azarov et al. | |
| 4,173,725 A | 11/1979 | Asai et al. | |
| 4,204,096 A | 5/1980 | Barcus et al. | |
| 4,398,325 A | 8/1983 | Piaget et al. | |
| 4,666,595 A | 5/1987 | Graham | |
| 4,699,588 A | 10/1987 | Zinn et al. | |
| 4,743,361 A | 5/1988 | Schram | |
| 4,759,775 A | 7/1988 | Peterson et al. | |
| 4,983,189 A | 1/1991 | Peterson et al. | |
| 5,225,089 A | 7/1993 | Benes et al. | |
| 5,371,429 A | 12/1994 | Manna | |
| 5,395,592 A | 3/1995 | Bolleman et al. | |
| 5,443,985 A | 8/1995 | Lu et al. | |
| 5,452,267 A | 9/1995 | Spevak | |
| 5,484,537 A | 1/1996 | Whitworth | |
| 5,527,460 A * | 6/1996 | Trampler | B01D 21/283 209/155 |
| 5,560,362 A | 10/1996 | Sliwa, Jr. et al. | |
| 5,594,165 A | 1/1997 | Madanshetty | |
| 5,604,301 A | 2/1997 | Mountford et al. | |
| 5,626,767 A | 5/1997 | Trampler et al. | |
| 5,688,405 A | 11/1997 | Dickinson et al. | |
| 5,711,888 A | 1/1998 | Trampler et al. | |
| 5,831,166 A | 11/1998 | Kozuka et al. | |
| 5,902,489 A | 5/1999 | Yasuda et al. | |
| 5,912,182 A | 6/1999 | Coakley et al. | |
| 5,951,456 A | 9/1999 | Scott | |
| 6,090,295 A | 7/2000 | Raghavarao et al. | |
| 6,166,231 A | 12/2000 | Hoeksema | |
| 6,205,848 B1 | 3/2001 | Faber et al. | |
| 6,216,538 B1 | 4/2001 | Yasuda et al. | |
| 6,332,541 B1 * | 12/2001 | Coakley | B01J 19/10 209/160 |
| 6,391,653 B1 | 5/2002 | Letcher et al. | |
| 6,487,095 B1 | 11/2002 | Malik et al. | |
| 6,592,821 B1 | 7/2003 | Wada et al. | |
| 6,649,069 B2 | 11/2003 | DeAngelis | |
| 6,763,722 B2 | 7/2004 | Fjield et al. | |
| 6,881,314 B1 | 4/2005 | Wang et al. | |
| 6,929,750 B2 | 8/2005 | Laurell et al. | |
| 6,936,151 B1 | 8/2005 | Lock et al. | |
| 7,010,979 B2 | 3/2006 | Scott | |
| 7,061,163 B2 | 6/2006 | Nagahara et al. | |
| 7,081,192 B1 | 7/2006 | Wang et al. | |
| 7,093,482 B2 | 8/2006 | Berndt | |
| 7,108,137 B2 | 9/2006 | Lal et al. | |
| 7,150,779 B2 | 12/2006 | Meegan, Jr. | |
| 7,186,502 B2 | 3/2007 | Vesey | |
| 7,191,787 B1 | 3/2007 | Redeker et al. | |
| 7,331,233 B2 | 2/2008 | Scott | |
| 7,340,957 B2 | 3/2008 | Kaduchak et al. | |
| 7,373,805 B2 | 5/2008 | Hawkes et al. | |
| 7,541,166 B2 | 6/2009 | Belgrader et al. | |
| 7,601,267 B2 | 10/2009 | Haake et al. | |
| 7,673,516 B2 | 3/2010 | Janssen et al. | |
| 7,837,040 B2 | 11/2010 | Ward et al. | |
| 7,846,382 B2 | 12/2010 | Strand et al. | |
| 7,968,049 B2 | 6/2011 | Takahashi et al. | |
| 8,080,202 B2 | 12/2011 | Takahashi et al. | |
| 8,256,076 B1 | 9/2012 | Feller | |
| 8,266,950 B2 | 9/2012 | Kaduchak et al. | |
| 8,273,253 B2 | 9/2012 | Curran | |
| 8,273,302 B2 | 9/2012 | Takahashi et al. | |
| 8,309,408 B2 | 11/2012 | Ward et al. | |
| 8,319,398 B2 | 11/2012 | Vivek et al. | |
| 8,334,133 B2 | 12/2012 | Fedorov et al. | |
| 8,387,803 B2 | 3/2013 | Thorslund et al. | |
| 2002/0134734 A1 | 9/2002 | Campbell et al. | |
| 2003/0195496 A1 | 10/2003 | Maguire | |
| 2003/0209500 A1 | 11/2003 | Kock et al. | |
| 2003/0230535 A1 | 12/2003 | Affeld et al. | |
| 2005/0196725 A1 | 9/2005 | Fu | |
| 2006/0037915 A1 | 2/2006 | Strand et al. | |
| 2007/0272618 A1 | 11/2007 | Gou et al. | |
| 2007/0284299 A1 | 12/2007 | Xu et al. | |
| 2008/0217259 A1 | 9/2008 | Siversson | |
| 2009/0029870 A1 | 1/2009 | Ward et al. | |
| 2009/0045107 A1 | 2/2009 | Ward et al. | |
| 2009/0053686 A1 | 2/2009 | Ward et al. | |
| 2009/0098027 A1 | 4/2009 | Tabata et al. | |
| 2009/0178716 A1 | 7/2009 | Kaduchak et al. | |
| 2009/0194420 A1 | 8/2009 | Mariella, Jr. et al. | |
| 2009/0295505 A1 | 12/2009 | Mohammadi et al. | |
| 2010/0000945 A1 | 1/2010 | Gavalas | |
| 2010/0078384 A1 | 4/2010 | Yang | |
| 2010/0124142 A1 | 5/2010 | Laugharn et al. | |
| 2010/0192693 A1 | 8/2010 | Mudge et al. | |
| 2010/0193407 A1 | 8/2010 | Steinberg et al. | |
| 2010/0206818 A1 | 8/2010 | Leong et al. | |
| 2010/0255573 A1 | 10/2010 | Bond et al. | |
| 2010/0317088 A1 | 12/2010 | Radaelli et al. | |
| 2010/0323342 A1 | 12/2010 | Gonzalez Gomez et al. | |
| 2010/0330633 A1 | 12/2010 | Walther et al. | |
| 2011/0024335 A1 | 2/2011 | Ward et al. | |
| 2011/0092726 A1 | 4/2011 | Clarke | |
| 2011/0123392 A1 | 5/2011 | Dionne et al. | |
| 2011/0154890 A1 | 6/2011 | Holm et al. | |
| 2011/0166551 A1 | 7/2011 | Schafer | |
| 2011/0262990 A1 | 10/2011 | Wang et al. | |
| 2011/0281319 A1 | 11/2011 | Swayze et al. | |
| 2011/0309020 A1 | 12/2011 | Rietman et al. | |
| 2012/0088295 A1 | 4/2012 | Yasuda et al. | |
| 2012/0328477 A1 | 12/2012 | Dionne et al. | |
| 2012/0329122 A1 | 12/2012 | Lipkens et al. | |
| 2013/0277317 A1 | 10/2013 | LoRicco et al. | |
| 2014/0011240 A1 | 1/2014 | Lipkens et al. | |

FOREIGN PATENT DOCUMENTS

| | | |
|---|---|---|
| EP | 1 254 669 B1 | 11/2002 |
| GB | 2 420 510 A | 5/2006 |
| JP | 9-136090 | 5/1997 |
| WO | WO 87/07178 A1 | 12/1987 |
| WO | WO 90/05008 | 3/1990 |
| WO | WO 02/072234 A1 | 9/2002 |
| WO | WO 2009/111276 A1 | 9/2009 |
| WO | WO 2009/144709 A1 | 12/2009 |
| WO | WO 2010/024753 A1 | 4/2010 |
| WO | WO 2011/023949 A2 | 3/2011 |
| WO | WO 2011/027146 A2 | 3/2011 |
| WO | WO 2011/161463 A2 | 12/2011 |

OTHER PUBLICATIONS

Alvarez et al.; Shock Waves, vol. 17, No. 6, pp. 441-447, 2008.
Benes et al.; Ultrasonic Separation of Suspended Particles, 2001 IEEE Ultrasonics Symposium; Oct. 7-10, 2001; pp. 649-659; Atlanta, Georgia.
Castro; Tunable gap and quantum quench dynamics in bilayer graphene; Jul. 13, 2010; Mathematica Summer School.
Cravotto et al.; Ultrasonics Sonochemistry, vol. 15, No. 5, pp. 898-902, 2008.
Garcia-Lopez, et al; Enhanced Acoustic Separation of Oil-Water Emulsion in Resonant Cavities. The Open Acoustics Journal. 2008, vol. 1, pp. 66-71.
Gor'kov; On the forces acting on a small particle in an acoustical field in an ideal fluid; Soy. Phys. Dokl.; vol. 6, pp. 773-775; 1962.
Hill et al.; Ultrasonic Particle Manipulation; Microfluidic Technologies for Miniaturized Analysis Systems, Jan. 2007, pp. 359-378.
Kuznetsova et al.; Microparticle concentration in short path length ultrasonic resonators: Roles of radiation pressure and acoustic streaming; Journal of the Acoustical Society of America, American Institute of Physics for the Acoustical Society of America, vol. 116, No. 4, Oct. 1, 2004, pp. 1956-1966, DOI: 1.1121/1.1785831.
Latt et al.; Ultrasound-membrane hybrid processes for enhancement of filtration properties; Ultrasonics sonochemistry 13.4 (2006): 321-328.

(56) References Cited

OTHER PUBLICATIONS

Lipkens et al.; Frequency sweeping and fluid flow effects on particle trajectories in ultrasonic standing waves; Acoustics 08, Paris, Jun. 29-Jul. 4, 2008.
Lipkens et al.; Prediction and measurement of particle velocities in ultrasonic standing waves; J. Acoust. Soc. Am., 124 No. 4, pp. 2492 (A) 2008.
Lipkens et al.; Separation of micron-sized particles in macro-scale cavities by ultrasonic standing waves; Presented at the International Congress on Ultrasonics, Santiago; Jan. 11-17, 2009.
Lipkens et al.; The effect of frequency sweeping and fluid flow on particle trajectories in ultrasonic standing waves; IEEE Sensors Journal, vol. 8, No. 6, pp. 667-677, 2008.
Meribout et a.; An Industrial-Prototype Acoustic Array for Real-Time Emulsion Layer Detection in Oil Storage Tanks; IEEE Sensors Journal, vol. 9, No. 12, Dec. 2009.
Nilsson et al.; Review of cell and particle trapping in microfluidic systems; Department of Measurement Technology and Industrial Electrical Engineering, Div. of Nanobiotechnology, Lund University, P.O. Box 118. Lund, Sweden, Analytica Chimica Acta 649, Jul. 14, 2009, pp. 141-157.
Pangu et al.; Droplet transport and coalescence kinetics in emulsions subjected to acoustic fields; Ultrasonics 46, pp. 289-302 (2007).
Ponomarenko et al.; Density of states and zero Landau level probed through capacitance of graphene; Nature Nanotechnology Letters, Jul. 5, 2009; DOI: 10.1038/NNANO.2009.177.
Seymour et al, J. Chem. Edu., 1990, 67(9), p. 763, published Sep. 1990.
Annex to Form PCT/ISA/206—Communication Relating to the Results of the Partial International Search Report, dated Jul. 18, 2013.
European Search Report of European Application No. 11769474.5 Dated Oct. 10, 2012.
International Search Report and Written Opinion dated Dec. 20, 2011, for corresponding PCT application No. PCT/US2011/032181.
International Search Report and Written Opinion dated Feb. 27, 2012, for PCT application No. PCT/US2011/040787.
International Search Report and Written Opinion of International Application No. PCT/US2013/037404 Dated Jun. 21, 2013.
International Search Report and Written Opinion of International Application No. PCT/US2013/050729 Dated Sep. 25, 2013.
International Search Report for corresponding PCT Application Serial No. PCT/US2014/015382 dated May 6, 2014.
Phys. Org. "Engineers develop revolutionary nanotech water desalination membrane." Nov. 6, 2006. http://phys.org/news82047372.html.
"Proceedings of the Acoustics 2012 Nantes Conference," Apr. 23-27, 2012, Nantes, France, pp. 278-282.
Sony New Release: <http://www.sony.net/SonyInfo/News/Press/201010/10-137E/index.html>.

\* cited by examiner

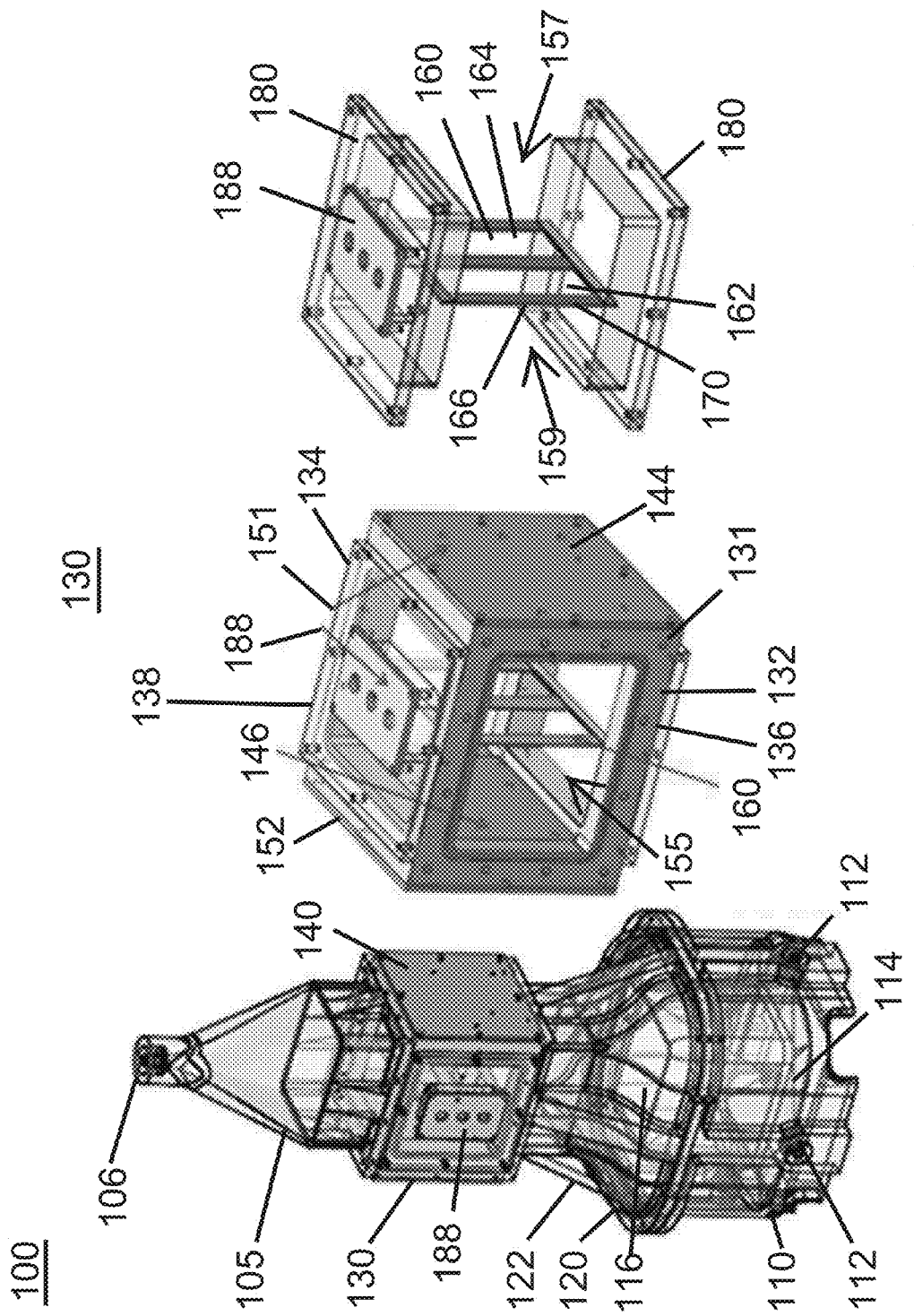

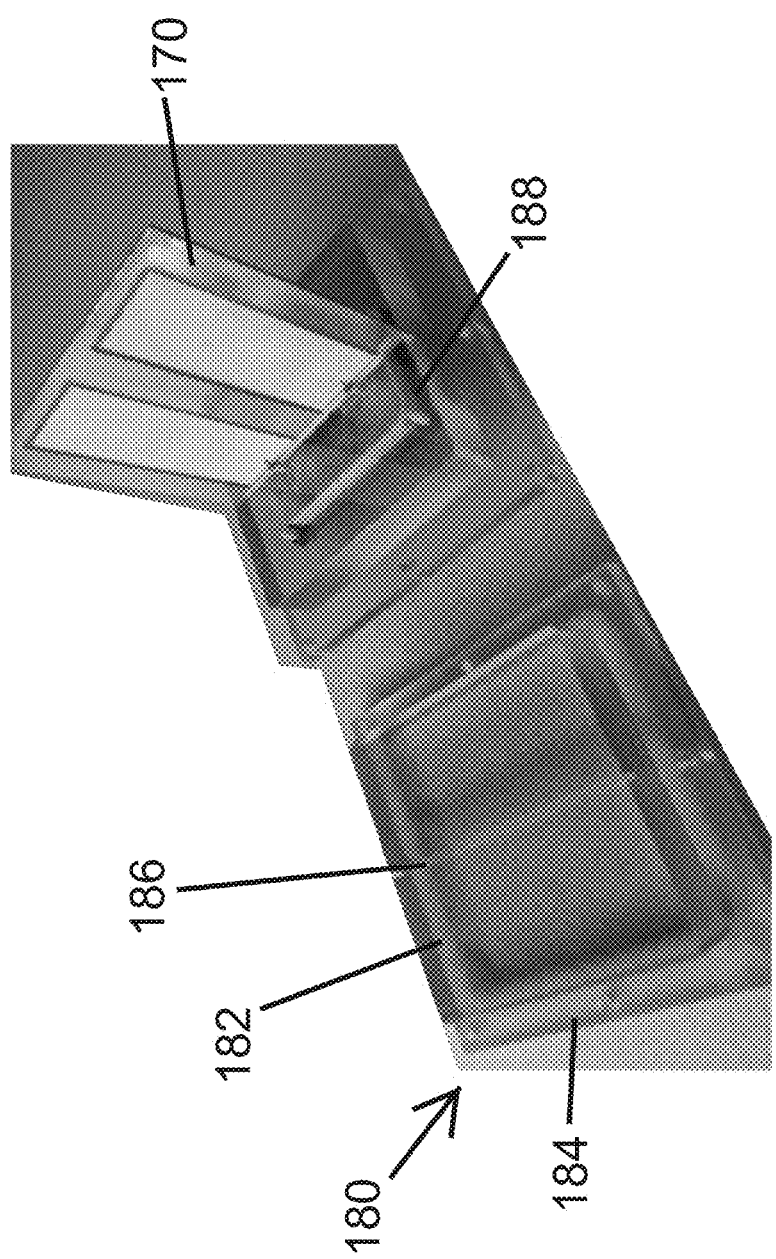

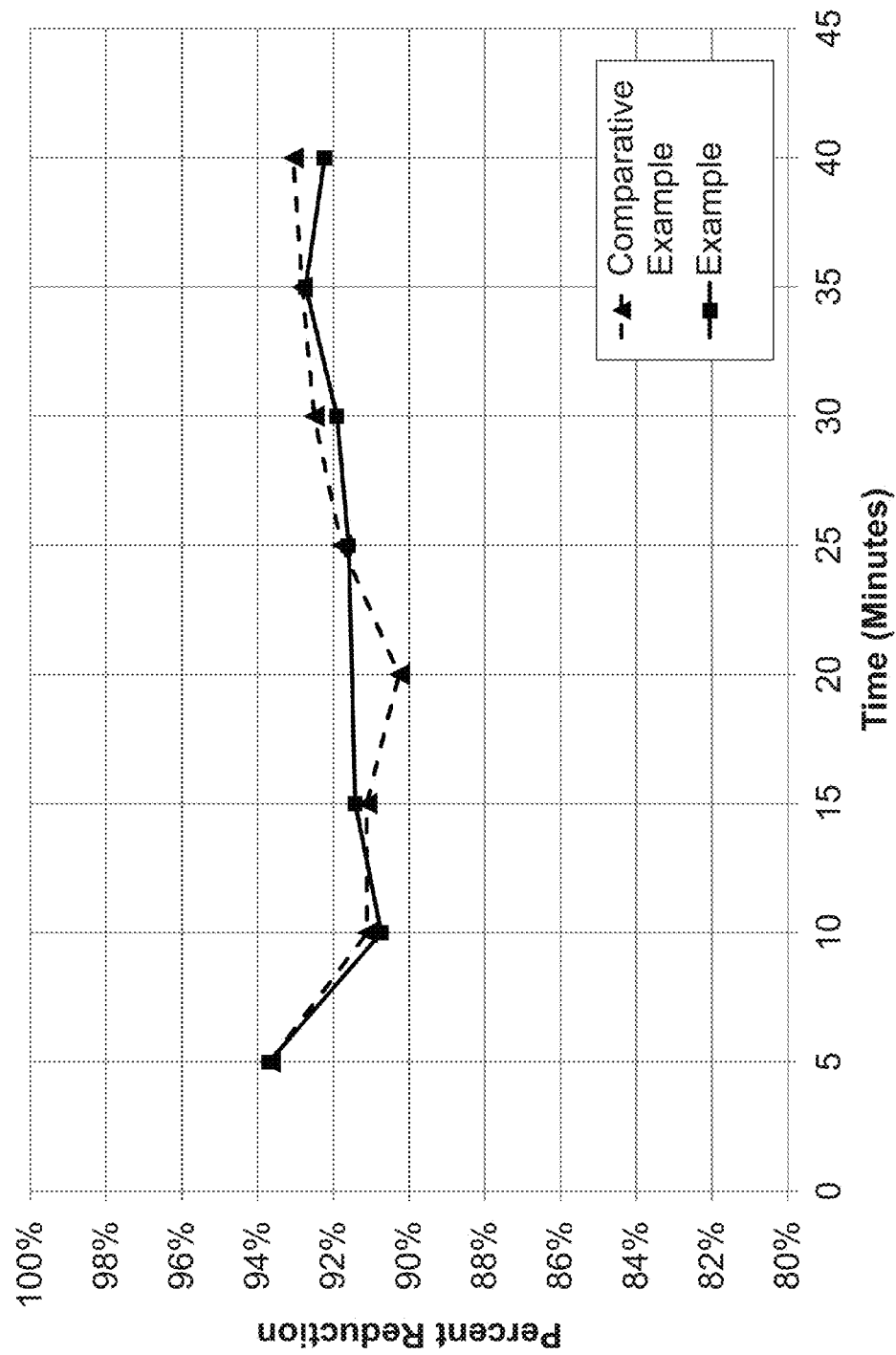

ACOUSTOPHORESIS DEVICE WITH DUAL ACOUSTOPHORETIC CHAMBER

CROSS-REFERENCE TO RELATED APPLICATIONS

This application claims priority to U.S. Provisional Patent Application Ser. No. 61/925,171, filed Jan. 8, 2014. The disclosures of this application is hereby fully incorporated by reference in its entirety.

BACKGROUND

The ability to separate a particle/fluid mixture into its separate components is desirable in many applications. Acoustophoresis is the separation of particles using high intensity sound waves, and without the use of membranes or physical size exclusion filters. It has been known that high intensity standing waves of sound can exert forces on particles in a fluid when there is a differential in both density and compressibility, otherwise known as the contrast factor. A standing wave has a pressure profile which appears to "stand" still in time. The pressure profile in a standing wave contains areas of net zero pressure at its nodes and anti-nodes. Depending on the density and compressibility of the particles, they will be trapped at the nodes or anti-nodes of the standing wave. The higher the frequency of the standing wave, the smaller the particles that can be trapped.

Conventional acoustophoresis devices have had limited efficacy due to several factors including heat generation, limits on fluid flow, and the inability to capture different types of materials. In particular, heat generation can be deleterious to materials in the fluid stream, particularly in biopharmaceutical applications when materials such as Chinese hamster ovary (CHO) cells and proteins and monoclonal antibodies expressed therefrom are present in the fluid stream.

In this regard, an ultrasonic transducer including a piezoelectric element has typically been used to generate ultrasonic waves. The transducer is generally mounted into the wall of a chamber, with a reflector mounted in the opposite wall. The face of the reflector is parallel to the face of the piezoelectric element, maximizing reflection of the incident wave generated from the piezoelectric element to form the standing wave. Heat is generated by the piezoelectric element during operation when performing acoustophoresis. It would be desirable to provide alternative designs that minimize heat generation.

BRIEF SUMMARY

The present disclosure relates to acoustophoretic systems that include a piezoelectric element in the middle of a flow path, rather than to one side of the flow path. This permits both sides of the piezoelectric element to generate an acoustic standing wave, rather than only one side of the element. This also permits both sides to be exposed to the fluid stream and the resulting cooling effect, mitigating heat buildup in the piezoelectric element. This device can be used to separate particles from a particle/fluid mixture. Either a new mixture with an increased concentration of particles can be obtained, or the separated particles themselves can be obtained. In more specific embodiments, the particles are biological cells, such as Chinese hamster ovary (CHO) cells, NS0 hybridoma cells, baby hamster kidney (BHK) cells, and human cells. Several different types of modules and overall systems are described herein.

Disclosed in various embodiments herein is an acoustophoresis device, comprising: a device inlet permitting fluid flow into the device; a device outlet permitting fluid egress from the device; and an acoustic chamber located in a fluid path between the device inlet and the device outlet. The acoustic chamber comprises: a first end and a second end opposite the first end; a piezoelectric element running between the first end and the second end, and separating the acoustic chamber into a first flow chamber and a second flow chamber, the piezoelectric element having a first face and a second face; a first reflector opposite the first face of the piezoelectric element, the first flow chamber being located between the first reflector and the first face; and a second reflector opposite the second face of the piezoelectric element, the second flow chamber being located between the second reflector and the second face.

The acoustic chamber can further comprise: a holding plate that holds the piezoelectric element, and two bracket plates having a slot for maintaining the holding plate in a fixed location in the acoustic chamber.

The piezoelectric element may include a plurality of piezoelectric crystals. Generally, the piezoelectric element is adapted to create a multi-dimensional standing wave in the first flow chamber and the second flow chamber. In more specific embodiments, different standing waves (e.g. of different frequencies) are generated in the first flow chamber and the second flow chamber by the piezoelectric element.

In some embodiments, the acoustophoresis device is shaped such that fluid flows into the device through the device inlet, into the first end of the acoustic chamber, then flows in parallel through the first flow chamber and the second flow chamber, out of the acoustic chamber through the second end of the acoustic chamber, and out of the device through the device outlet. The acoustophoresis device can further comprise a contoured nozzle wall between the device inlet and the acoustic chamber.

In other embodiments, the acoustophoresis device is shaped such that fluid flows into the device through the device inlet, then travels through the acoustic chamber in a U-shaped path from the first end of the acoustic chamber to the second end through the first flow chamber and then back to the first end through the second flow chamber, then exits the flow chamber through the first end of the acoustic chamber and exits the device through the device outlet. In such embodiments, the second end of the acoustic chamber may lead to a well that tapers downwards in cross-sectional area from a single inlet to a vertex, and a drain line connecting the vertex to a port for recovering material collected in the well.

Also disclosed are methods of separating particles from a host fluid, comprising: flowing a mixture of the host fluid and the particles through an acoustophoresis device as described above, having a first flow chamber and a second flow chamber. A pulsed voltage signal drives the piezoelectric element to create multidimensional standing waves in the first flow chamber and the second flow chamber to separate the particles from the host fluid.

The multi-dimensional standing waves may result in an acoustic radiation force having an axial force component and a lateral force component that are of the same order of magnitude, in both the first flow chamber and the second flow chamber.

In particular embodiments, the particles are Chinese hamster ovary (CHO) cells, NS0 hybridoma cells, baby hamster kidney (BHK) cells, or human cells.

The pulsed voltage signal may have a sinusoidal, square, sawtooth, or triangle waveform. The pulsed voltage signal may have a frequency of 500 kHz to 10 MHz. The pulsed voltage signal can be driven with amplitude or frequency modulation start/stop capability to eliminate acoustic streaming.

In particular embodiments, the mixture of the host fluid and the particles has a Reynolds number of 1500 or less prior to entering the acoustic chamber. Sometimes, the mixture flows vertically upwards, and the particles sink down to a collection duct.

Also disclosed in various embodiments herein is an acoustophoresis device, comprising: a device inlet permitting fluid flow into the device; a device outlet permitting fluid egress from the device; and an acoustic chamber located in a fluid path between the device inlet and the device outlet. The acoustic chamber comprises a plurality of piezoelectric elements running between the first end and the second end; and a plurality of reflectors. Each piezoelectric element has a first face and a second face; and each element is located between two reflectors.

These and other non-limiting characteristics are more particularly described below.

BRIEF DESCRIPTION OF THE DRAWINGS

The following is a brief description of the drawings, which are presented for the purposes of illustrating the exemplary embodiments disclosed herein and not for the purposes of limiting the same.

FIG. 1 is an exterior perspective view of an acoustophoresis device including the "dual acoustophoresis chamber" of the present disclosure. Visible in this view is a connector panel for powering the piezoelectric element.

FIG. 2 is a perspective view of the dual acoustophoresis chamber only, with the connector panel at the top of the figure.

FIG. 3 is a perspective view of the holding plate that holds the piezoelectric element located between two bracket plates which hold the holding plate in place within the acoustic chamber.

FIG. 4 is a picture showing the holding plate and the bracket plates. The piezoelectric element is made up of two separate rectangular piezoelectric crystals.

FIG. 12 is a graph showing device efficiency over time, showing equivalent operation over time for both the conventional system and the dual acoustophoresis chamber of the present disclosure.

DETAILED DESCRIPTION

Figure 5:
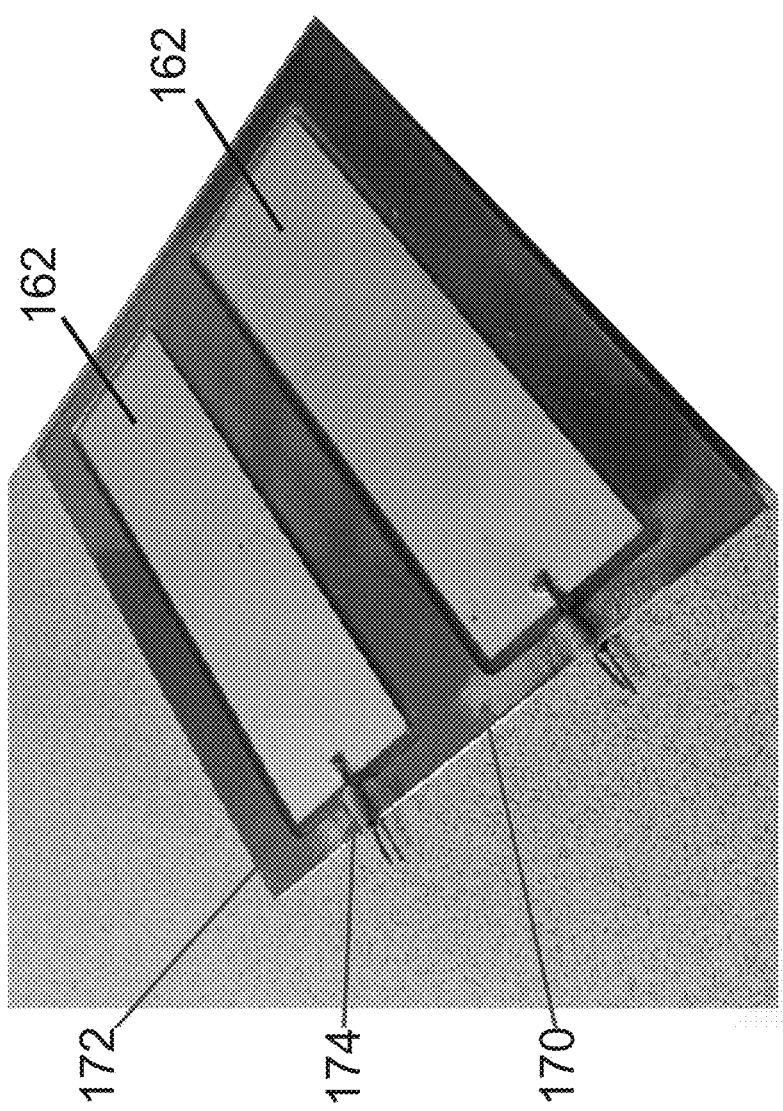
FIG. 5 is a picture showing the holding plate and the piezoelectric element in more detail.

The present disclosure may be understood more readily by reference to the following detailed description of desired embodiments and the examples included therein. In the following specification and the claims which follow, reference will be made to a number of terms which shall be defined to have the following meanings.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function. Furthermore, it should be understood that the drawings are not to scale.

The singular forms "a," "an," and "the" include plural referents unless the context clearly dictates otherwise.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named components/steps and permit the presence of other components/steps. However, such description should be construed as also describing compositions or processes as "consisting of" and "consisting essentially of" the enumerated components/steps, which allows the presence of only the named components/steps, along with any impurities that might result therefrom, and excludes other components/steps.

Numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values).

The term "about" can be used to include any numerical value that can vary without changing the basic function of that value. When used with a range, "about" also discloses the range defined by the absolute values of the two endpoints, e.g. "about 2 to about 4" also discloses the range "from 2 to 4." The term "about" may refer to plus or minus 10% of the indicated number.

It should be noted that many of the terms used herein are relative terms. For example, the terms "upper" and "lower" are relative to each other in location, i.e. an upper component is located at a higher elevation than a lower component in a given orientation, but these terms can change if the device is flipped. The terms "inlet" and "outlet" are relative to a fluid flowing through them with respect to a given structure, e.g. a fluid flows through the inlet into the structure and flows through the outlet out of the structure. The terms "upstream" and "downstream" are relative to the direction in which a fluid flows through various components, i.e. the flow fluids through an upstream component prior to flowing through the downstream component. It should be noted that in a loop, a first component can be described as being both upstream of and downstream of a second component.

The terms "horizontal" and "vertical" are used to indicate direction relative to an absolute reference, i.e. ground level. However, these terms should not be construed to require structures to be absolutely parallel or absolutely perpendicular to each other. For example, a first vertical structure and a second vertical structure are not necessarily parallel to each other. The terms "upwards" and "downwards" are also relative to an absolute reference; an upwards flow is always against the gravity of the earth.

The present application refers to "the same order of magnitude." Two numbers are of the same order of magnitude if the quotient of the larger number divided by the smaller number is a value less than 10.

The acoustophoretic separation technology of the present disclosure employs ultrasonic standing waves to trap, i.e., hold stationary, secondary phase particles in a host fluid stream. This is an important distinction from previous approaches where particle trajectories were merely altered by the effect of the acoustic radiation force. The scattering of the acoustic field off the particles results in a three dimensional acoustic radiation force, which acts as a three-dimensional trapping field. The acoustic radiation force is proportional to the particle volume (e.g. the cube of the radius) when the particle is small relative to the wavelength. It is proportional to frequency and the acoustic contrast factor. It also scales with acoustic energy (e.g. the square of the acoustic pressure amplitude). For harmonic excitation, the sinusoidal spatial variation of the force is what drives the particles to the stable positions within the standing waves. When the acoustic radiation force exerted on the particles is stronger than the combined effect of fluid drag force and buoyancy and gravitational force, the particle is trapped within the acoustic standing wave field. This results in concentration, agglomeration and/or coalescence of the trapped particles. Additionally, secondary inter-particle forces, such as Bjerkness forces, aid in particle agglomeration. Heavier-than-the-host-fluid (i.e. denser than the host fluid) particles are separated through enhanced gravitational settling.

One specific application for the acoustophoresis device is in the processing of bioreactor materials. It is important to be able to filter all of the cells and cell debris from the expressed materials that are in the fluid stream. The expressed materials are composed of biomolecules such as recombinant proteins or monoclonal antibodies, and are the desired product to be recovered. Through the use of acoustophoresis, the separation of the cells and cell debris is very efficient and leads to very little loss of the expressed materials. This is an improvement over current filtration processes (depth filtration, tangential flow filtration, centrifugation), which show limited efficiencies at high cell densities, so that the loss of the expressed materials in the filter beds themselves can be up to 5% of the materials produced by the bioreactor. The use of mammalian cell cultures including Chinese hamster ovary (CHO), NS0 hybridoma cells, baby hamster kidney (BHK) cells, and human cells has proven to be a very efficacious way of producing/expressing the recombinant proteins and monoclonal antibodies required of today's pharmaceuticals. The filtration of the mammalian cells and the mammalian cell debris through acoustophoresis aids in greatly increasing the yield of the bioreactor.

In this regard, the contrast factor is the difference between the compressibility and density of the particles and the fluid itself. These properties are characteristic of the particles and the fluid themselves. Most cell types present a higher density and lower compressibility than the medium in which they are suspended, so that the acoustic contrast factor between the cells and the medium has a positive value. As a result, the axial acoustic radiation force (ARF) drives the cells, with a positive contrast factor, to the pressure nodal planes, whereas cells or other particles with a negative contrast factor are driven to the pressure anti-nodal planes. The radial or lateral component of the acoustic radiation force helps trap the cells. The radial or lateral component of the ARF is larger than the combined effect of fluid drag force and gravitational force.

As the cells agglomerate at the nodes of the standing wave, there is also a physical scrubbing of the cell culture media that occurs whereby more cells are trapped as they come in contact with the cells that are already held within the standing wave. This generally separates the cells from the cell culture media. The expressed biomolecules remain in the nutrient fluid stream (i.e. cell culture medium).

Desirably, the ultrasonic transducer(s) generate a three-dimensional or multi-dimensional acoustic standing wave in the fluid that exerts a lateral force on the suspended particles to accompany the axial force so as to increase the particle trapping capabilities of the standing wave. Typical results published in literature state that the lateral force is two orders of magnitude smaller than the axial force. In contrast, the technology disclosed in this application provides for a lateral force to be of the same order of magnitude as the axial force.

It is also possible to drive multiple ultrasonic transducers with arbitrary phasing. In other words, the multiple transducers may work to separate materials in a fluid stream while being out of phase with each other. Alternatively, a single ultrasonic transducer that has been divided into an ordered array may also be operated such that some components of the array will be out of phase with other components of the array.

Three-dimensional (3-D) or multi-dimensional acoustic standing waves are generated from one or more piezoelectric transducers, where the transducers are electrically or mechanically excited such that they move in a multi-excitation mode. The types of waves thus generated can be characterized as composite waves, with displacement profiles that are similar to leaky symmetric (also referred to as compressional or extensional) Lamb waves. The waves are leaky because they radiate into the water layer, which result in the generation of the acoustic standing waves in the water layer. Symmetric Lamb waves have displacement profiles that are symmetric with respect to the neutral axis of the piezoelectric element, which causes multiple standing waves to be generated in a 3-D space. Through this manner of wave generation, a higher lateral trapping force is generated than if the piezoelectric transducer is excited in a "piston" mode where only a single, planar standing wave is generated. Thus, with the same input power to a piezoelectric transducer, the 3-D or multi-dimensional acoustic standing waves can have a higher lateral trapping force which may be up to and beyond 10 times stronger than a single acoustic standing wave generated in piston mode.

It may be necessary, at times, due to acoustic streaming, to modulate the frequency or voltage amplitude of the standing wave. This may be done by amplitude modulation and/or by frequency modulation. The duty cycle of the propagation of the standing wave may also be utilized to achieve certain results for trapping of materials. In other words, the acoustic beam may be turned on and shut off at different frequencies to achieve desired results.

Some of the variables that are involved in the generation of a standing wave using piezoelectric crystals are voltage input, the Q factor of the piezoelectric crystal, the impedance of the full transducer that incorporates the piezoelectric crystal, and the temperature or heat generated by the piezoelectric crystal/transducer during the operation of the unit when performing acoustophoresis. As previously discussed, heat can be deleterious to materials in the fluid, such as biological cells or products. Prior devices have used various methods and fluid flow patterns to dissipate heat generated during acoustophoresis, or have modulated perturbation of the piezoelectric crystal to mitigate heat input into the system.

The present disclosure relates to acoustophoretic devices where the piezoelectric element that generates the standing wave is placed in the volume of the acoustic chamber, such that a fluid/particle mixture flows on both sides of the piezoelectric element and standing waves can be generated on both sides of the piezoelectric element. This may also be referred to as a "dual acoustophoresis chamber". The cooling effect of fluid flow on both sides mitigates heat buildup that may occur in the piezoelectric element. The fluid can be a liquid (e.g. water) or can be a gas (e.g. air).

FIG. 1 is an exterior perspective view of a basic acoustophoresis device 100 that includes the dual acoustophoresis chamber. The basic device here is illustrated as being formed from separate components. These components include an inlet module 110, a connecting module 120, the acoustic chamber 130, and an outlet module 105. Two exterior walls of the acoustic chamber can be seen. On one wall is a reflector 144, and on the other wall is a connector panel 188 for powering the piezoelectric element (not visible) inside the acoustic chamber.

In FIG. 1, fluid flow is upwards. Briefly, the inlet module contains inlets 112 that feed into an annular plenum 114. A fluid/particle mixture is pumped in through the inlets. The mixture flows upwards under pressure into the connecting module 120, which has a contoured nozzle wall 122 that reduces the cross-section of the fluid flow path. As fluid continues to be pumped into the flow path, eventually the inlet module 110 and the acoustic chamber 130 are filled with fluid, and the fluid pressure rises high enough that fluid will flow out through the outlet 106 at the top of the device. The particles within the ultrasonic standing wave collect or agglomerate, and eventually grow to a size where gravity overcomes the acoustic force of the standing wave, and the particle aggregates then fall/sink through a collection duct 116 that is surrounded by the annular plenum 114. The particles can then be collected, either as a more concentrated fluid/particle mixture or simply the particles themselves are collected.

FIG. 2 is a perspective view of the acoustic chamber of FIG. 1. The acoustic chamber 130 includes a housing 131 having a first end 132 and a second end 134 which are located at opposite ends of the housing. Here, the housing is in the shape of a cube having four side walls 151, 152 (third and fourth side walls not visible), a first wall 136, and a second wall 138. However, the exterior shape of the module is not particularly relevant, and could be for example cylindrical. The first end and the second end of the housing can be considered as defining a z-axis. The four opposing side walls can be considered as corresponding to opposite directions along the x-y axes of the housing.

A flow channel 155 is defined between the first end 132 and the second end 134 of the housing. Put another way, an opening is present in both the first wall and the second wall, and a bore joins the two openings together, such that fluid can flow through the housing from between the first end and the second end. As illustrated here, the bore has a rectangular cross-section. The piezoelectric element is located within the volume of the flow channel. As illustrated here, there are two reflectors 144, 146, which are located on opposite sides of the piezoelectric element 160. The faces of the two reflectors are parallel to the two faces of the piezoelectric element. Each reflector is solid or flexible, and can be made of a high acoustic impedance material such as steel or tungsten, providing good reflection. Also visible is the connector panel 188 on another side wall of the housing. The connectors can be any suitable type, such as BNC connectors.

FIG. 3 is a perspective view of specific portions of the acoustic chamber. In this regard, the piezoelectric element 160 is located within the volume of the acoustic chamber. The combination of the piezoelectric element 160, the first reflector 144, and the second reflector 146 divides the acoustic chamber 130 and the flow channel 155 into a first flow chamber 157 and a second flow chamber 159. As depicted here, the piezoelectric element 160 is comprised of two rectangular piezoelectric crystals 162. Generally, any number of piezoelectric crystals can be used to make up the piezoelectric element, and those crystals can be oriented in any direction relative to each other. The piezoelectric crystals are held in place by a holding plate 170. The holding plate is itself held in place by two bracket plates 180.

The piezoelectric element 160 has a first face 164 and a second face 166. Examining FIG. 2 and FIG. 3 together, there is a first reflector 144 opposite the first face 164. The first flow chamber 157 is located between the first reflector and the first face. Similarly, there is a second reflector 146 opposite the second face 166, with the second flow chamber 159 being located therebetween. Please note the location of the reflectors 144, 146 is based on the location of the piezoelectric element 160; the reflectors do not need to be set in the walls of the housing, as will be seen further below. However, generally, the faces of the piezoelectric element are parallel to the walls of the acoustic chamber, and reflectors are also located in opposite walls of the acoustic chamber, the reflectors being parallel to the faces of the piezoelectric element.

FIG. 4 is a photograph showing a bracket plate (left side) 180 separated from the holding plate 170. It is noted that the bracket plates are solid pieces; fluid does not flow through them. As depicted here, each bracket plate 180 includes a central block 182 and an edge plate 184 around its periphery, to connect the bracket plate to the housing. The edge plate 184 may not be needed in different embodiments, for example where the housing is of a different shape such that only the central block 182 is needed to connect to the housing. The central block 182 of each bracket plate also contains at least one slot 186, into which an edge of the holding plate 170 is inserted to fix the holding plate in a stationary position within the volume of the acoustic chamber. As discussed further below, a reflector can also be fixed within a slot. The bracket plate on the right side holds the holding plate 170, and also provides the connector panel 188 for powering the piezoelectric element.

FIG. 5 is a photograph showing the holding plate 170 for the piezoelectric element. Here, the holding plate is made of steel, and provides space for two piezoelectric crystals 162. A silicon potting layer/gasket 172 is located around each piezoelectric crystal, and holds the crystal within the frame provided by the holding plate. Electrical leads 174 are soldered to one end of each crystal as well. With this construction, it is intended that the fluid/particle mixture cannot flow through the holding plate from the first flow chamber to the second flow chamber. Rather, the fluid/particle mixture flows from one end of the acoustic chamber and through one flow chamber, then exit the other end of the acoustic chamber.

It is noted that although the holding plate and the bracket plates are described as separate pieces here, they could be made as one integral piece.

The piezoelectric crystal is usually made of PZT-8 (lead zirconate titanate). Such crystals may have a 1 inch length/width and a nominal 2 MHz resonance frequency. Each piezoelectric element can be formed from only one crystal, or be formed from multiple crystals that each act as a separate ultrasonic transducer and are either controlled by one or multiple amplifiers. This allows each crystal to vibrate in one of its eigenmodes with a high Q-factor. The vibrating crystal is directly exposed to the fluid flowing through the acoustic chamber.

The lack of backing on the piezoelectric crystal(s) (e.g. making the crystal air backed) also permits each piezoelectric crystal to vibrate at higher order modes of vibration with little damping (e.g. higher order modal displacement). The higher order the mode shape of the crystal, the more nodal lines the crystal has. The higher order modal displacement of the crystal creates more trapping lines, although the correlation of trapping line to node is not necessarily one to one, and driving the crystal at a higher frequency will not necessarily produce more trapping lines.

Placing the piezoelectric crystals in direct contact with the fluid also contributes to the high Q-factor by avoiding dampening and energy absorption effects. In embodiments, the piezoelectric crystal may be coated to prevent the PZT, which contains lead, contacting the host fluid. This may be desirable in, for example, biological applications such as separating blood. Such applications might use a wear layer such as chrome, electrolytic nickel, or electroless nickel. Chemical vapor deposition could also be used to apply a layer of poly(p-xylylene) (e.g. Parylene) or other polymer. Organic and biocompatible coatings such as silicone or polyurethane are also usable as a wear surface.

It is noted that the standing waves generated on the first face and the second face of the piezoelectric element may be different, depending on how the piezoelectric crystals are perturbated by the electrical input. In particular embodiments, the standing waves differ from each other by at least 50 kilohertz (kHz).

Figure 6:
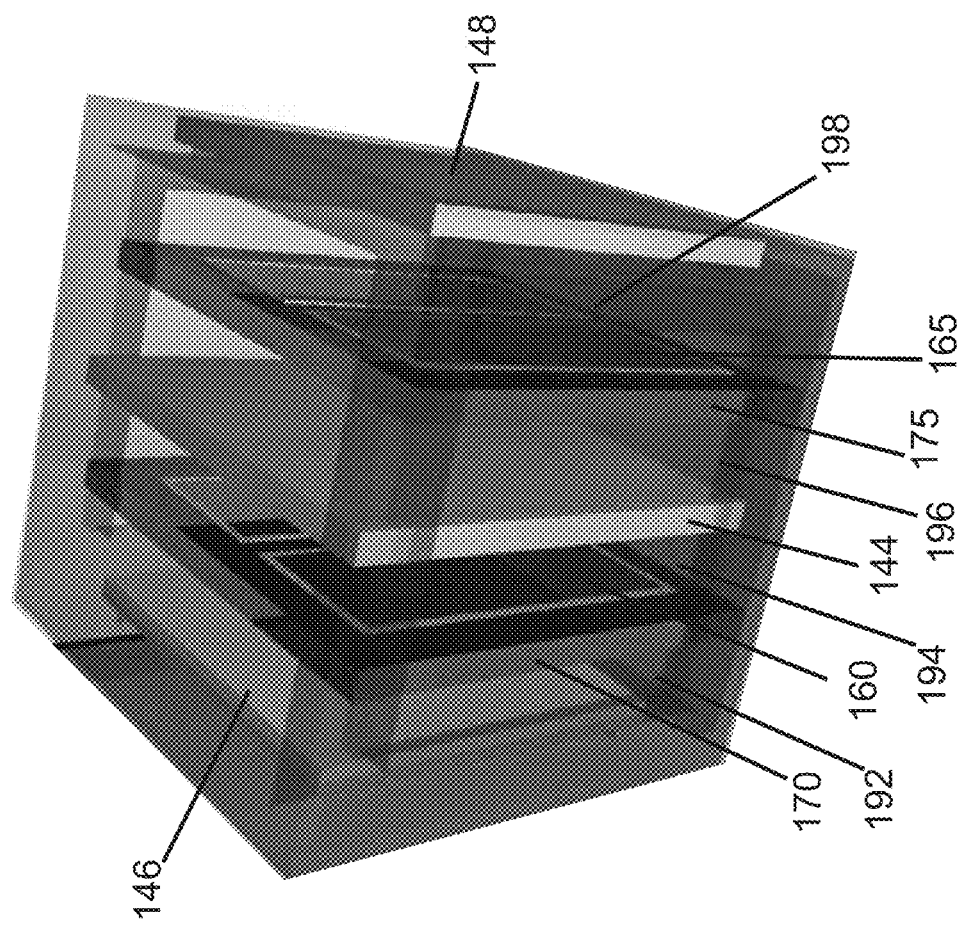
FIG. 6 is a perspective view of a second exemplary embodiment. Here, two piezoelectric elements are placed within the volume of the acoustic chamber. There are a total of three reflectors in the acoustic chamber, two on opposite walls and one in the middle of the acoustic chamber. The acoustic chamber contains four different flow paths through which a fluid/particle mixture can flow.

Generally speaking, the present disclosure relates to the use of the piezoelectric element to generate standing waves on both sides, rather than on only one side as has been done in conventional devices. The present disclosure contemplates that more than one such piezoelectric element can be present within the acoustic chamber. FIG. 6 is a depiction of such an embodiment. In this embodiment, there are two holding plates 170, 175 for two piezoelectric elements 160, 165. There are now three total reflectors in this embodiment. Compared to FIG. 2, the reflector 144 can also be considered a central reflector located between the two piezoelectric elements. The reflector 146 and central reflector 144 are located on opposite sides of the first piezoelectric element 170. The central reflector 144 and third reflector 148 are located on opposite sides of the second piezoelectric element 172. The faces of the reflectors are parallel to the faces of the piezoelectric elements. The central reflector 144 reflects waves generated by both piezoelectric elements 160, 165.

There are now four different flow chambers by which fluid can flow past the piezoelectric elements. A first flow chamber 192 is located between the reflector 146 and the first piezoelectric element 160. A second flow chamber 194 is located between the central reflector 144 and the first piezoelectric element 160. A third flow chamber 196 is located between the central reflector 144 and the second piezoelectric element 165. A fourth flow chamber 198 is located between the reflector 148 and the second piezoelectric element 165. It is noted that in this particular embodiment, the bracket plates 180 would include three slots, two slots for the holding plates 170, 175 and one slot for the central reflector 144.

It is contemplated that any number of piezoelectric elements can be placed within the volume of the acoustic chamber, for example three, four, six, eight, ten, twelve, or even more, as desired by the user. For n piezoelectric elements, there must be (n+1) reflectors in the acoustic chamber, with each piezoelectric element being located between two reflectors. Again, the faces of the piezoelectric element should be parallel to a face of each reflector. The practical number of piezoelectric elements and reflectors is thus constrained by the volume of the acoustic chamber.

Figure 7:
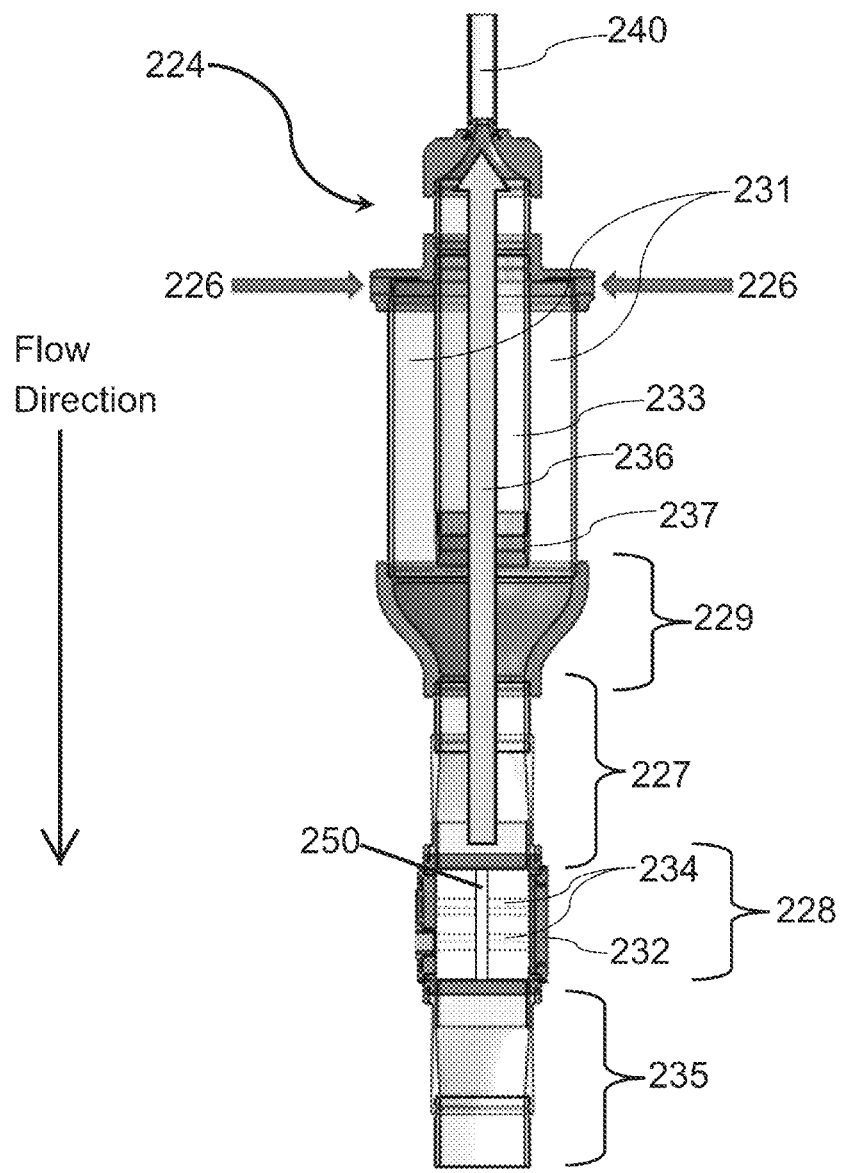
FIG. 7 shows an exemplary acoustophoretic separator for use with the dual acoustophoresis chamber of the present disclosure. Here, fluid flows from the top of the separator through the chamber and out the bottom of the separator.
Figure 8:
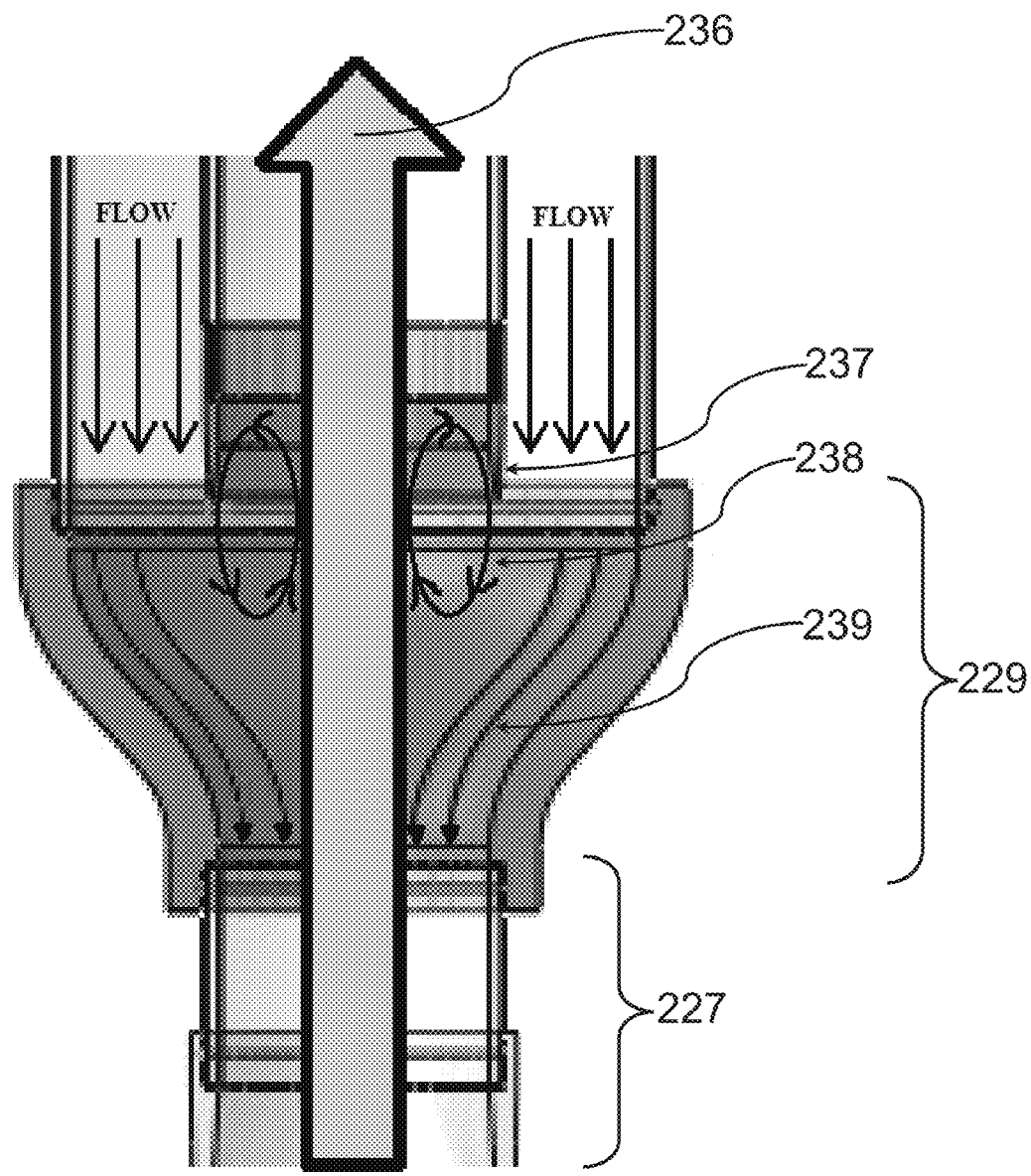
FIG. 8 is a magnified view of fluid flow near the intersection of the contoured nozzle wall and the collection duct in the separator of FIG. 7.

FIG. 7 and FIG. 8 are side views of one type of acoustophoretic device in which the dual acoustophoresis chamber can be used. The device is shown here in an orientation where the flow direction is downwards, which is used for separating less-dense particles from the host fluid. However, the device may be essentially turned upside down to allow separation of particles which are heavier than the host fluid (similar to FIG. 1). Instead of a buoyant force in an upward direction, the weight of the agglomerated particles due to gravity pulls them downward. It should be noted that this embodiment is depicted as having an orientation in which fluid flows vertically. However, it is also contemplated that fluid flow may be in a horizontal direction, or at an angle.

A particle-containing fluid flows into the device through inlets 226 into an annular plenum 231. The annular plenum has an annular inner diameter and an annular outer diameter. Two inlets are visible in this illustration, though it is contemplated that any number of inlets may be provided as desired. In particular embodiments, four inlets are used. The inlets are radially opposed and oriented.

A contoured nozzle wall 229 reduces the outer diameter of the flow path in a manner that generates higher velocities near the wall region and reduces turbulence, producing near plug flow as the fluid velocity profile develops, i.e. the fluid is accelerated downward in the direction of the centerline with little to no circumferential motion component and low flow turbulence. This generates a chamber flow profile that is optimum for acoustic separation and particle collection. The fluid passes through connecting duct 227 and into the acoustic chamber 228.

As seen in the zoomed-in contoured nozzle 229 in FIG. 8, the nozzle wall also adds a radial motion component to the suspended particles, moving the particles closer to the centerline of the apparatus and generating more collisions with rising, buoyant agglomerated particles. This radial motion will allow for optimum scrubbing of the particles from the fluid in the connecting duct 227 prior to reaching the separation chamber. The contoured nozzle wall 229 directs the fluid in a manner that generates large scale vortices at the entrance of the collection duct 233 to also enhance particle collection. Generally, the flow area of the device 224 is designed to be continually decreasing from the annular plenum 231 to the acoustic chamber 228 to assure low turbulence and eddy formation for better particle separation, agglomeration, and collection. The nozzle wall has a wide end and a narrow end. The term scrubbing is used to describe the process of particle/droplet agglomeration, aggregation, clumping or coalescing, that occurs when a larger particle/droplet travels in a direction opposite to the fluid flow and collides with smaller particles, in effect scrubbing the smaller particles out of the suspension.

Returning to FIG. 7, the acoustic chamber 228 includes reflectors 232 on opposite sides of the chamber, and a piezoelectric element within the chamber. In use, standing waves 234 are created between the piezoelectric element and each reflector 232. These standing waves can be used to agglomerate particles, and this orientation is used to agglomerate particles that are buoyant (e.g. oil). The fluid/particle mixture flows through both flow chambers in the same direction, i.e. in parallel. Fluid, containing residual particles, then exits or egresses the device through outlet 235.

As the buoyant particles agglomerate, they eventually overcome the combined effect of the fluid flow drag forces and acoustic radiation force, and their buoyant force 236 is sufficient to cause the buoyant particles to rise upwards. In this regard, a collection duct 233 is surrounded by the annular plenum 231. The larger particles will pass through this duct and into a collection chamber 240. This collection chamber can also be part of an outlet duct. The collection duct and the flow outlet are on opposite ends of the device.

It should be noted that the buoyant particles formed in the separation chamber 228 subsequently pass through the connecting duct 227 and the nozzle wall 229. This causes the incoming flow from the annular plenum to flow over the rising agglomerated particles due to the inward radial motion imparted by the nozzle wall. This allows the rising particles to also trap smaller particles in the incoming flow, increasing scrubbing effectiveness. The length of the connecting duct 227 and the contoured nozzle wall 229 thus increase scrubbing effectiveness. Especially high effectiveness is found for particles with a size of 0.1 microns to 20 microns, where efficiency is very low for conventional methods.

The device of FIG. 7 is shaped such that fluid flows into the device through the device inlet, into the first end of the acoustic chamber, then flows in parallel through the first flow chamber and the second flow chamber, out of the acoustic chamber through the second end of the acoustic chamber, and out of the device through the device outlet. This design provides an optimized velocity profile with low flow turbulence at the inlet to the acoustic chamber 228, a scrubbing length before the flow chamber to enhance particle agglomeration and/or coalescence before acoustic separation, and the use of the collection vortices to aid particle removal at the collection duct 233.

Figure 9:
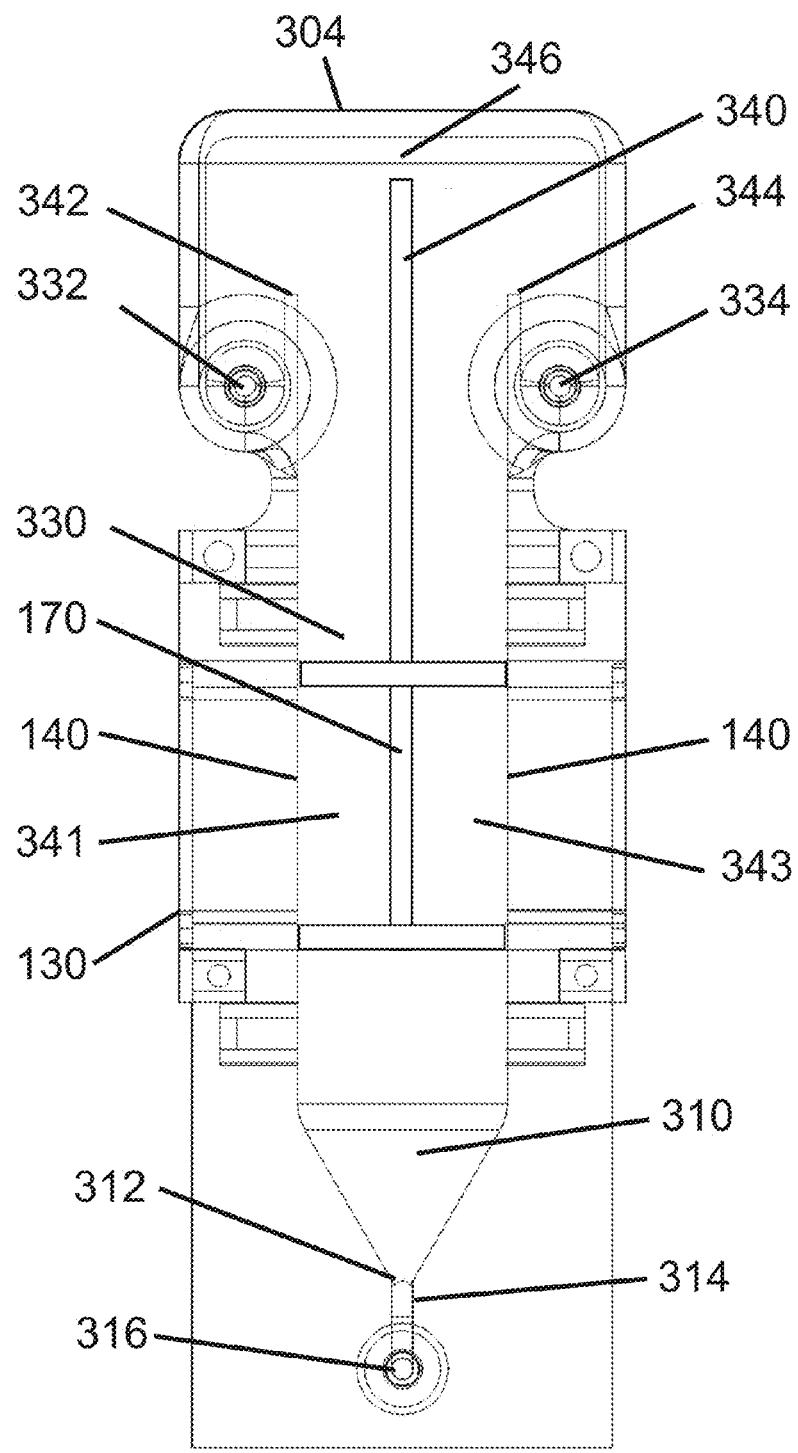
FIG. 9 is a front view of a second exemplary acoustophoretic device in which fluid flows in through an inlet at the top of the device, and then travels in a U-shaped flow path through the acoustophoretic chamber and then exits through an outlet at the top of the device as well. Separated particles are collected through a well at the bottom of the device.

An alternative device design that can incorporate the dual acoustophoresis chamber is shown in FIG. 9. In this device, the inlet and outlet are both located at the same end of the device (here, the upper end). A fluid/particle mixture is pumped in through the inlet port 332. The mixture flows downwards via gravity through the acoustic chamber, where the particles are trapped and held by the ultrasonic standing wave. As fluid continues to be pumped into the flow path, eventually the device is filled with fluid, and the fluid pressure rises high enough that fluid will flow out through the outlet 334 at the top of the device. The particles within the ultrasonic standing waves collect or agglomerate, and eventually grow to a size where gravity overcomes the acoustic force of the standing wave, and the particle aggregates then fall/sink into a collection well 310 that tapers downwards in cross-sectional size to a vertex 312. A drain line 314 connects the vertex 312 to a port 316 where the concentrated particles can be drawn out of the well.

As illustrated here, a wall 340 is located in the flow channel 330 between the inlet 332 and the outlet 334. Fluid thus flows from the inlet downwards through the acoustic chamber through the first flow chamber, then back upwards through the second flow chamber and then to the outlet. The cross-sectional area of the first flow chamber can be smaller than, equal to, or greater than the cross-sectional area of the second flow chamber. As illustrated here, the wall (of which the holding plate is a part) is placed so that the cross-sectional area 341 of the flow channel for the inlet port is smaller than the cross-sectional area 343 of the flow channel for the outlet port.

Also visible is a first retainer wall 342 adjacent the inlet and a second retainer wall 344 adjacent the outlet. As seen here, the inlet 332 and the outlet 334 are located relatively close to the middle of the front wall, and are spaced apart from the upper end 304 of the device. Incoming fluid must flow towards the upper end 304 and then over the first retainer wall 342 before flowing into the acoustic chamber. Similarly, fluid coming back from the acoustic chamber must flow over the second retainer wall 344 before exiting through the outlet 334. This construction provides a means by which the turbulence of incoming fluid can be reduced, so that the particles trapped in the acoustic standing wave in the acoustic chamber are not disrupted or washed out of the standing wave before aggregating to a sufficient size.

As also depicted here, in some embodiments, the wall 340 is spaced apart from the upper end 304 of the housing. This gap 346 forms and acts as a pressure relief passage between the inlet 332 and the outlet 334, for example in case the flow path is inadvertently blocked.

As a result of this construction, fluid flows into the device through the device inlet, then travels through the acoustic chamber in a U-shaped path from the first end of the acoustic chamber to the second end through the first flow chamber and then back to the first end through the second flow chamber, then exits the flow chamber through the first end of the acoustic chamber and exits the device through the device outlet.

The various components of the acoustic chamber containing the piezoelectric element can be made of any appropriate material, such as polycarbonate, acrylic (e.g. polymethyl methacrylate), or glass (e.g. soda lime or borosilicate), or polypropylene. It is generally desirable for the material to be somewhat transparent, so that a clear window can be produced and the internal flow channels and flow paths can be seen during operation of the acoustophoresis device/system.

Various coatings may be used on the internal flow channels of the modules. Such coatings include epoxies, for example epichlorohydrin bisphenol-A crosslinked with an amine or a polyamide; or polyurethane coatings, for example a polyester polyol crosslinked with aliphatic isocyanates, or a silicone coating or a polyoxyalkylene coating. Such coatings are useful for producing a smooth surface and/or reducing surface tension, permitting cells to slide better under the influence of gravity along the flow channel surface and into desired locations (such as the collection well).

The flow rate of the acoustophoretic device must be controlled so that gravity can act on particle aggregates. In this regard, it is contemplated that the particle/fluid mixture passing in/out of the flow path in the acoustophoretic device can flow at rates of up to about 100 milliliters per minute (ml/min).

In the present systems, the system is operated at a voltage such that the particles are trapped in the ultrasonic standing waves, i.e., remain in a stationary position. The particles are collected in along well defined trapping lines, separated by half a wavelength. Within each nodal plane, the particles are trapped in the minima of the acoustic radiation potential. The axial component of the acoustic radiation force drives the particles, with a positive contrast factor, to the pressure nodal planes, whereas particles with a negative contrast factor are driven to the pressure anti-nodal planes. The radial or lateral component of the acoustic radiation force is the force that traps the particle. The radial or lateral component of the acoustic radiation force is on the same order of magnitude as the axial component of the acoustic radiation force. As discussed above, the lateral force can be increased by driving the piezoelectric element in higher order mode shapes, as opposed to a form of vibration where the piezoelectric element effectively moves as a piston having a uniform displacement. The acoustic pressure is proportional to the driving voltage. The electrical power is proportional to the square of the voltage.

In embodiments, the pulsed voltage signal driving the piezoelectric element can have a sinusoidal, square, sawtooth, or triangle waveform; and have a frequency of 500 kHz to 10 MHz. The pulsed voltage signal can be driven with pulse width modulation, which produces any desired waveform. The pulsed voltage signal can also have amplitude or frequency modulation start/stop capability to eliminate streaming.

The size, shape, and thickness of the piezoelectric crystal determines the displacement at different frequencies of excitation, which in turn affects separation efficiency. Typically, the piezoelectric element is operated at frequencies near the thickness resonance frequency (half wavelength). Gradients in displacement typically result in more places for particles to be trapped. Higher order modal displacements generate three-dimensional acoustic standing waves with strong gradients in the acoustic field in all directions, thereby creating equally strong acoustic radiation forces in all directions, leading to multiple trapping lines, where the number of trapping lines correlate with the particular mode shape of the piezoelectric element.

Figure 10:
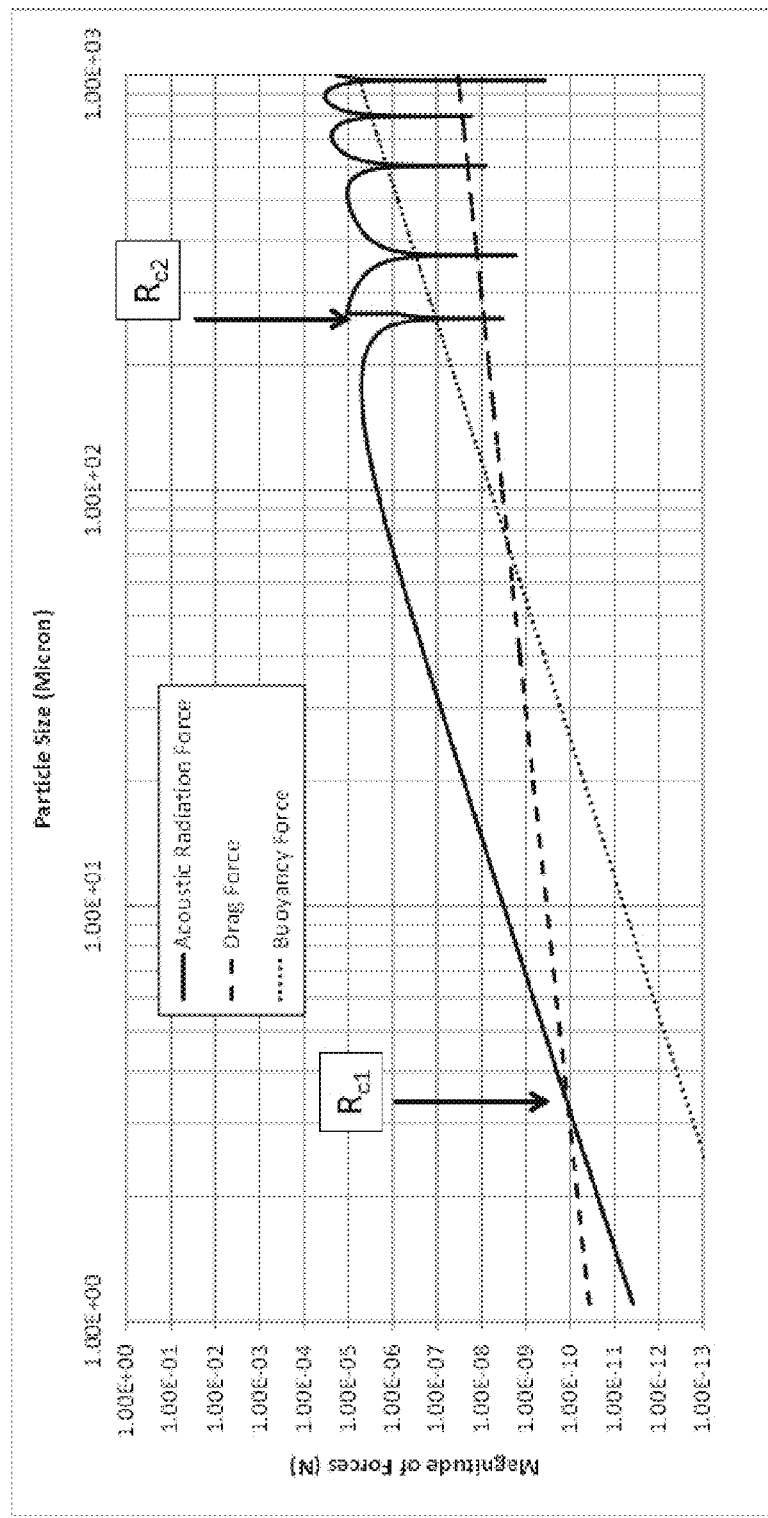
FIG. 10 is a graph showing the relationship of the acoustic radiation force, buoyancy force, and Stokes' drag force to particle size. The horizontal axis is in microns (μm) and the vertical axis is in Newtons (N).

FIG. 10 is a lin-log graph (linear y-axis, logarithmic x-axis) that shows the scaling of the acoustic radiation force, fluid drag force, and buoyancy force with particle radius. Calculations are done for a typical SAE-30 oil droplet used in experiments. The buoyancy force is a particle volume dependent force, and is therefore negligible for particle sizes on the order of micron, but grows, and becomes significant for particle sizes on the order of hundreds of microns. The fluid drag force scales linearly with fluid velocity, and therefore typically exceeds the buoyancy force for micron sized particles, but is negligible for larger sized particles on the order of hundreds of microns. The acoustic radiation force scaling acts differently. When the particle size is small, the acoustic trapping force scales with the volume of the particle. Eventually, when the particle size grows, the acoustic radiation force no longer increases with the cube of the particle radius, and will rapidly vanish at a certain critical particle size. For further increases of particle size, the radiation force increases again in magnitude but with opposite phase (not shown in the graph). This pattern repeats for increasing particle sizes.

Initially, when a suspension is flowing through the system with primarily small micron sized particles, it is necessary for the acoustic radiation force to balance the combined effect of fluid drag force and buoyancy force for a particle to be trapped in the standing wave. In FIG. 10 this happens for a particle size of about 3.5 micron, labeled as $R_{c1}$. The graph then indicates that all larger particles will be trapped as well. Therefore, when small particles are trapped in the standing wave, particles coalescence/clumping/aggregation/agglomeration takes place, resulting in continuous growth of effective particle size. As the particle size grows, the acoustic radiation force reflects off the particle, such that large particles will cause the acoustic radiation force to decrease. Particle size growth continues until the buoyancy force becomes dominant, which is indicated by a second critical particle size, $R_{c2}$, at which size the particles will rise or sink, depending on their relative density with respect to the host fluid. As the particles rise or sink, they no longer reflect the acoustic radiation force, so that the acoustic radiation force then increases. Not all particles will drop out, and those remaining particles will continue to grow in size as well. This phenomenon explains the quick drops and rises in the acoustic radiation force beyond size $R_{c2}$. Thus, FIG. 10 explains how small particles can be trapped continuously in a standing wave, grow into larger particles or clumps, and then eventually will rise or settle out because of increased buoyancy force.

The following examples are for purposes of further illustrating the present disclosure. The examples are merely illustrative and are not intended to limit devices made in accordance with the disclosure to the materials, conditions, or process parameters set forth therein.

EXAMPLES

A conventional acoustophoresis device was used as a Comparative Example. This device used an acoustic chamber in which the ultrasonic transducer was located on one wall of the chamber, and a reflector was located on the opposite wall. The transducer had one piezoelectric crystal of dimensions 1 inch×3 inches.

An acoustophoresis device of the present disclosure is labeled as Example. This device used an acoustic chamber in which the piezoelectric crystal was mounted in the middle of the acoustic chamber. Two reflectors were located on opposite walls, parallel to the face of the one piezoelectric crystal. This piezoelectric crystal also had dimensions 1 inch×3 inches.

Figure 11:
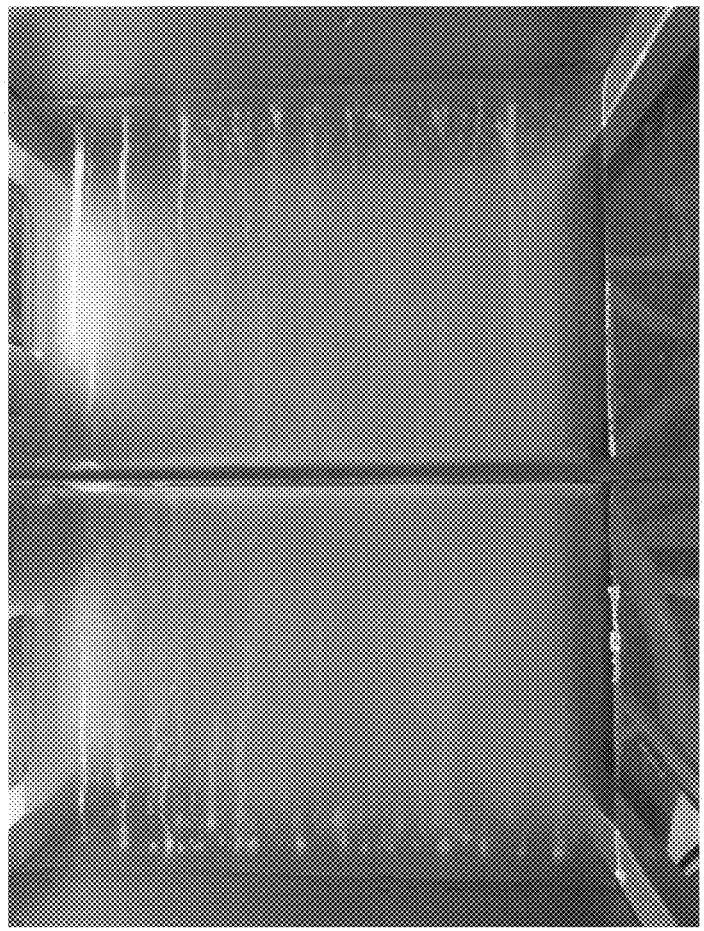
FIG. 11 is a picture showing the dual acoustophoresis chamber of the present disclosure being operated. The trapping lines are visible.

The two devices were then operated with a yeast slurry as the feed input. The slurry contained 0.5% solids. The devices were operated over 40 minutes of operation. FIG. 11 is a picture illustrating operation of the dual acoustophoresis chamber. The trapping lines generated by the piezoelectric element located in the middle of the chamber are visible.

Samples were periodically taken from the acoustic chamber. After 40 minutes of operation, the concentrate, permeate, and retentate were measured as well. The concentrate was the portion exiting the device that contained the concentrated yeast, along with some fluid. The permeate was the filtered portion exiting the device, which was mostly liquid with a much lower concentration of yeast. The retentate was the remaining substance left in the device after operation. The results are provided in the following table.

|  | Comparative Example | Example |
| --- | --- | --- |
| Feed Turbidity (NTU) | 876 | 978 |
| Retentate Turbidity (NTU) | 1345 | 1708 |
| Concentrate Turbidity (NTU) | 3620 | 2164 |
| Permeate Turbidity (NTU) | 71.6 | 88.1 |
| Overall Efficiency (%) | 92 | 91 |

As seen from these results, the efficiency of the dual acoustophoretic chamber, wherein the piezoelectric element is located within the volume of the chamber and divides the chamber into multiple flow chambers, is about equal to that of the conventional system illustrated by the Comparative Example.

FIG. 12 is a chart showing the efficiency in terms of percent reduction in turbidity from the feed, over time. As seen here, the present device is just as efficient and effective over time as the conventional system.

The present disclosure has been described with reference to exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. An acoustophoresis device, comprising:
a device inlet permitting fluid flow into the device;
a device outlet permitting fluid egress from the device; and
an acoustic chamber located in a fluid path between the device inlet and the device outlet, the acoustic chamber comprising:
  a first ultrasonic transducer including a first face and a second face;
  a first reflector opposite the first face of the first ultrasonic transducer, a first flow chamber being located between the first reflector and the first face of the first ultrasonic transducer; and
  a second reflector opposite the second face of the first ultrasonic transducer, a second flow chamber being located between the second reflector and the second face of the first ultrasonic transducer;
  wherein the first ultrasonic transducer is adapted to create a first multi-dimensional acoustic standing wave in the first flow chamber and a second multi-dimensional acoustic standing wave in the second flow chamber, and wherein secondary phase particles in a host fluid are trapped in the multi-dimensional acoustic standing waves and agglomerate into larger particles that continuously settle out at a critical particle size due to enhanced gravitational settling.

2. The acoustophoresis device of claim 1, wherein the acoustic chamber further comprises: a holding plate that holds the first ultrasonic transducer, and two bracket plates having a slot for maintaining the holding plate in a fixed location in the acoustic chamber.

3. The acoustophoresis device of claim 1, wherein the first ultrasonic transducer further comprises a piezoelectric element that includes a plurality of piezoelectric crystals.

4. The acoustophoresis device of claim 1, wherein the first multi-dimensional acoustic standing wave has the same frequency as, or a different frequency from, the second multi-dimensional acoustic standing wave.

5. The acoustophoresis device of claim 1, wherein the acoustophoresis device is shaped such that fluid flows into the device through the device inlet, into a first end of the acoustic chamber, then flows in parallel through the first flow chamber and the second flow chamber, out of the acoustic chamber through a second end of the acoustic chamber that is opposite the first end, and out of the device through the device outlet.

6. The acoustophoresis device of claim 1, further comprising a contoured nozzle wall between the device inlet and the acoustic chamber.

7. The acoustophoresis device of claim 1, wherein the acoustophoresis device is shaped such that fluid flows into the device through the device inlet, then travels through the acoustic chamber in a U-shaped path from a first end of the acoustic chamber to a second end through the first flow chamber and then back to the first end through the second flow chamber, then exits the flow chamber through the first end of the acoustic chamber and exits the device through the device outlet.

8. The acoustophoresis device of claim 7, wherein the second end of the acoustic chamber leads to a well that tapers downwards in cross-sectional area from a single inlet to a vertex, and a drain line connecting the vertex to a port for recovering material collected in the well.

9. The acoustophoresis device of claim 1, further comprising:
a second ultrasonic transducer including a first face and a second face, the first face of the second ultrasonic transducer facing the second reflector, and a third flow chamber being located between the second reflector and the first face of the second ultrasonic transducer; and
a third reflector opposite the second face of the second ultrasonic transducer, a fourth flow chamber being located between the third reflector and the second face of the second ultrasonic transducer.

10. A method of separating particles from a host fluid, comprising:
flowing a mixture of the host fluid and the particles through an acoustophoresis device that comprises:
  a device inlet permitting fluid flow into the device;
  a device outlet permitting fluid egress from the device; and
  an acoustic chamber located in a fluid path between the device inlet and the device outlet, the acoustic chamber comprising:
    a first ultrasonic transducer including a first face and a second face;
    a first reflector opposite the first face of the first ultrasonic transducer, a first flow chamber being located between the first reflector and the first face of the first ultrasonic transducer; and
    a second reflector opposite the second face of the first ultrasonic transducer, a second flow chamber being located between the second reflector and the second face of the first ultrasonic transducer; and
applying a drive signal to drive the first ultrasonic transducer to create multidimensional acoustic standing waves in the first flow chamber and the second flow chamber to separate the particles from the host fluid;
wherein the first ultrasonic transducer creates a first multi-dimensional acoustic standing wave in the first flow chamber and a second multi-dimensional acoustic standing wave in the second flow chamber, and wherein the particles in the host fluid are trapped in the multi-dimensional acoustic standing waves and agglomerate into larger particles that continuously settle out at a critical particle size due to enhanced gravitational settling.

11. The method of claim 10, wherein the multi-dimensional standing waves result in an acoustic radiation force having an axial force component and a lateral force component that are of the same order of magnitude, in both the first flow chamber and the second flow chamber.

12. The method of claim 10, wherein the particles are Chinese hamster ovary (CHO) cells, NS0 hybridoma cells, baby hamster kidney (BHK) cells, or human cells.

13. The method of claim 10, wherein the drive signal has a frequency of 500 kHz to 10 MHz.

14. The method of claim 10, wherein the drive signal is driven with amplitude or frequency modulation start/stop capability to eliminate acoustic streaming.

15. The method of claim 10, wherein the mixture of the host fluid and the particles has a Reynolds number of 1500 or less prior to entering the acoustic chamber.

16. The method of claim 10, wherein the first multi-dimensional acoustic standing wave has the same frequency as, or a different frequency from, the second multi-dimensional acoustic standing wave.

17. The method of claim 10, wherein the acoustophoresis device is shaped such that fluid flows into the device through the device inlet, into a first end of the acoustic chamber, then flows in parallel through the first flow chamber and the second flow chamber, out of the acoustic chamber through a second end of the acoustic chamber, and out of the device through the device outlet.

18. The method of claim 10, wherein the acoustophoresis device is shaped such that fluid flows into the device through the device inlet, then travels through the acoustic chamber in a U-shaped path from a first end of the acoustic chamber to a second end of the acoustic chamber through the first flow chamber and then back to the first end through the second flow chamber, then exits the flow chamber through the first end of the acoustic chamber and exits the device through the device outlet.

19. An acoustophoresis device, comprising:
a device inlet permitting fluid flow into the device;
a device outlet permitting fluid egress from the device; and
an acoustic chamber located in a fluid path between the device inlet and the device outlet, the acoustic chamber comprising:
a plurality of piezoelectric elements each piezoelectric element including a first face and a second face; and
a plurality of reflectors;
wherein each piezoelectric element is located between two reflectors, and wherein each piezoelectric element is adapted to create a first multi-dimensional acoustic standing wave from the first face and a second multi-dimensional acoustic standing wave from the second face, and wherein secondary phase particles in a host fluid are trapped in the multi-dimensional acoustic standing waves and agglomerate into larger particles that continuously settle out at a critical particle size due to enhanced gravitational settling.

20. The acoustophoresis device of claim 1, wherein the first face and the second face of the first ultrasonic transducer are both directly exposed to fluid flowing through the device.

21. The acoustophoresis device of claim 1, wherein the first face of the first ultrasonic transducer and the second face of the first ultrasonic transducer each have a wear layer.

22. The acoustophoresis device of claim 1, wherein the first ultrasonic transducer is made up of at least two piezoelectric crystals, wherein a first piezoelectric crystal forms the first face and a second piezoelectric crystal forms the second face.

* * * * *